United States Patent [19]

Firth et al.

[11] Patent Number: 4,718,405
[45] Date of Patent: Jan. 12, 1988

[54] ENHANCING L-GLUCOSE YIELD: EPIMERIZATION OF L-MANNOSE BY MOLYBDATE IN PRESENCE OF EPIMERIZATION INHIBITORS

[75] Inventors: Bruce E. Firth, Arlington Heights; Blaise J. Arena, Des Plaines, both of Ill.

[73] Assignee: UOP Inc., Des Plaines, Ill.

[21] Appl. No.: 29,286

[22] Filed: Mar. 23, 1987

Related U.S. Application Data

[63] Continuation-in-part of Ser. No. 889,154, Jul. 25, 1986, abandoned.

[51] Int. Cl.[4] .......................... C07H 1/00; C07H 1/06
[52] U.S. Cl. ................................. 127/46.1; 127/46.2; 536/124; 536/127
[58] Field of Search .................... 127/46.1, 46.2, 46.3; 536/1, 127, 124

[56] References Cited

U.S. PATENT DOCUMENTS

| | | | |
|---|---|---|---|
| 3,785,864 | 1/1974 | Lauer et al. | 127/46.2 |
| 4,029,878 | 6/1977 | Kruse | 127/30 |
| 4,471,114 | 9/1984 | Sherman et al. | 127/46.3 |

FOREIGN PATENT DOCUMENTS

| | | | |
|---|---|---|---|
| 149463 | 7/1973 | Czechoslovakia | 127/46.1 |
| 68696 | 6/1981 | Japan | 127/46.2 |

*Primary Examiner*—Curtis R. Davis
*Assistant Examiner*—Chung K. Pak
*Attorney, Agent, or Firm*—Thomas K. McBride; John F. Spears, Jr.; Eugene I. Snyder

[57] ABSTRACT

Although feedstocks of L-mannose prepared from hydrocyanation of L-arabinose contain inhibitors to the soluble molybdate-catalyzed epimerization of L-mannose to L-glucose, experimental conditions have been found which minimize such inhibition. A method is presented for improving the yield of L-glucose in a preparative route using hydrocyanation of L-arabinose as the entry to the L-hexoses by incorporating a soluble molybdate-catalyzed empimerrization stage conducted at a pH below 3.0.

5 Claims, 4 Drawing Figures

ENHANCING L-GLUCOSE YIELD: EPIMERIZATION OF L-MANNOSE BY MOLYBDATE IN PRESENCE OF EPIMERIZATION INHIBITORS

CROSS-REFERENCE TO RELATED APPLICATION

This application is a continuation-in-part of our co-pending application Ser. No. 889,154, filed Jul. 25, 1986, now abandoned, all of which is incorporated by reference.

BACKGROUND OF THE INVENTION

Present dietetic needs, predilections, and perceptions have led to the increased use of artificial sweeteners as a replacement for the "natural" sugars, including sucrose and fructose. Such artificial sweeteners are highly imperfect, including being under continual review for their long term physiological affects, yet their demand has grown unabated. Accompanying their growth as a commercial area with substantial economic impact has been a renewed emphasis on discovering and supplying new artificial sweeteners.

The ideal artificial sweetener would be noncaloric, noncariogenic, without detrimental physiological effects, and usable by diabetics. All these requirements would be met if a sweetener were not metabolized by humans and by flora which are found in the mouth and intestinal tract, and if the sweetener were either not absorbed by humans, or absorbed without effect on any internal organ. That is, the ideal sweetener should be excreted in the same form as when ingested. Another desirable feature is that it have bulk properties similar to sucrose so that it can be substituted for table sugar in many formulations. Recently, and perhaps belatedly, attention has turned toward the L-sugars as desirable artificial sweeteners. It has been known since at least 1946 that L-fructose is sweet (M. L. Wolfrom and A. Thompson, *J. Am. Chem. Soc.*, 68, 791,793 (1946)), and since at least 1890 that L-fructose is nonfermentable (E. Fischer, *Ber. Deutsch. Chem. Ges.*, 23, 370,389 (1890)), hence not metabolized by microorganisms generally metabolizing D-sugars. A reasonable, although not necessarily correct, inference is that it also is not metabolized by humans. Assuming that L-fructose is a sweet nonmetabolite it becomes obvious to use it as a noncaloric sweetener in many formulations. More recently Shallenberger and coworkers have demonstrated that many L-sugars have a sweetness comparable to their D-enantiomorphs. *Nature*, 221, 555 (1969). Cf. R. S. Shallenberger, "The Theory of Sweetness," in Sweeteners and Sweetness, pp 42–50, Edited by G. G. Birch and coworkers; R. S. Shallenberger and T. E. Acree in "The Handbook of Sensory Physiology," Vol. 4, pp 241–5, Edited by L. M. Beider (Springer Verlag, 1971).

Exploitation of the favorable properties of L-sugars is hindered by their relative unavailability. L-Fructose, for example, is not found to any significant extent in nature. This unavailability has spurred recent efforts in developing commercially feasible methods for preparing L-sugars in amounts necessary for their use as a staple of commerce. U.S. Pat. Nos. 4,371,616 and 4,421,568 describe a method of producing L-sugars, including L-idose and L-glucose, from the readily available D-glucose. Although the preparation of a number of L-sugars is described in U.S. Pat. No. 4,262,032 the focus seems to be on typical laboratory methods wholly unsuited for economical industrial production, in contrast to the process herein. U.S. Pat. No. 4,440,855 presents a flow scheme for the preparation of a mixture of L-glucose and L-mannose. The subject matter of U.S. Pat. No. 4,207,413 is L-sucrose, the enantiomer of ordinary table sugar, which can be hydrolyzed to afford L-fructose and L-glucose.

Where L-glucose is sought it is usually found in admixture with L-mannose. A process affording such a mixture of L-glucose and L-mannose is described in U.S. Pat. No. 4,581,447. Although separation of L-glucose from L-mannose can be effected in various ways the presence of mannose in the separation feedstock increases the cost of the purified L-glucose, with its cost increasing with increasing mannose content in the feedstock. Unfortunately, a mixture of L-glucose and L-mannose generally is produced under kinetic control with the L-mannose in preponderance, which imposes heavy cost penalties upon the production of relatively pure L-glucose. Since glucose is thermodynamically favored relative to mannose (Hayes et al., *J. Amer. Chem. Soc.*, 104, 6764 (1982)) it follows that if the separation feedstock would represent an equilibrium mixture of L-glucose and L-mannose, substantial and quite significant reductions in cost would accrue.

One could obtain an equilibrium mixture for separation either by producing the glucose-mannose mixture under equilibrium control, or by equilibrating a kinetically controlled product mixture. For various reasons the latter appeared the more promising route, which led to our evaluation of different equilibrating means. Given the intended use for L-glucose the requirements of minimum by-products and color body formation and minimum costs were mandatory.

The requisites for epimerizing L-mannose to L-glucose in a mixture containing both led to our focus on soluble molybdate as the equilibrating means. Bilik in Czechoslovak Certificate of Authorship 149,463 has demonstrated that molybdic acid epimerizes aqueous solutions of L-mannose to, supposedly, a 3:1 mixture of L-glucose:L-mannose. Hayes et al., op. cit., have elucidated some mechanistic aspects of this epimerization. In fact, molybdate readily epimerizes pure mannose. It was with great consternation to discover that under similar conditions molybdate failed to effect epimerization in a reaction product mixture of L-mannose and L-glucose! Further investigation into this unexpected phenomenon led to the cause of this failure, and continued investigation afforded a means of circumventing such problems.

SUMMARY OF THE INVENTION

The purpose of this invention is to provide a method of enhancing L-glucose yields obtained from a mixture of L-mannose and L-glucose arising from hydrocyanation of a pentose to a cyanohydrin, especially where followed by hydrogenation with concomitant hydrolysis of the cyanohydrin, where the mixture contains inhibitors to molybdate-catalyzed epimerization. An embodiment comprises conducting the epimerization at a pH below 3. In a more particular embodiment the epimerization pH is between about 1.3 and about 2.7. In a still more specific embodiment the epimerization is conducted at a temperature between about 80° C. and 100° C. at a pH between about 1.3 and 2.7.

DESCRIPTION OF THE INVENTION

Figure 1:
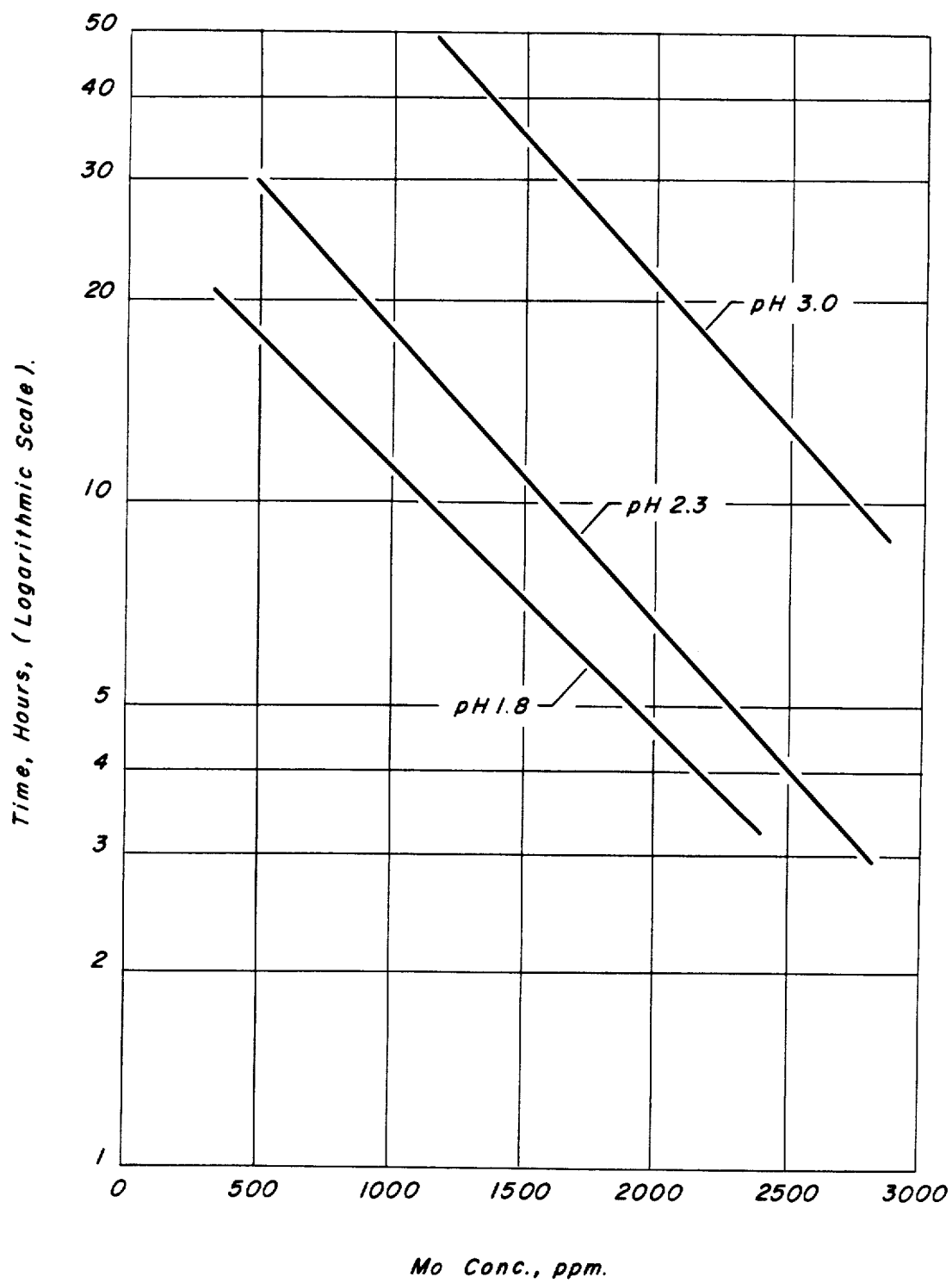
FIGS. 1 and 2 show the effect of pH on overcoming the poisoning effect of materials found in the epimerization feedstock.

Our invention is a method of increasing the yield of L-glucose from a mixture containing L-mannose and L-glucose with minor amounts of materials acting as inhibitors to molybdate-catalyzed epimerization of L-mannose. In particular, the aqueous solution containing L-mannose is a product mixture arising from hydrocyanation of L-arabinose. Hydrocyanation of the latter pentose affords a mixture of cyanohydrins which may be converted to hexoses by hydrogenation of the cyanohydrins accompanied by concomitant hydrolysis, with imines as the intermediate hydrogenation products, ultimately to afford a mixture of L-mannose and L-glucose. This entire reaction sequence hereafter will be referred to as hydrocyanation-hydrogenation-hydrolysis.

The L-hexoses generally are obtained by chain extension of an L-pentose, generally arabinose. A synthetic scheme directed toward the preparation of L-glucose usually produces a mixture both of L-glucose and L-mannose. Because the mixture generally reflects kinetic control of the products, mannose is the preponderant epimer. An example of a process incorporating the foregoing characteristics is described in U.S. Pat. No. 4,581,447. Equilibration of the mannose-glucose epimeric pair affords an approximately 2:1 ratio of glucose:mannose, obviously a highly desirable feature in reducing the cost associated with production of L-glucose.

Epimerization of an aqueous solution of pure D-mannose with molybdate at a concentration of 600 parts per million (ppm) and at 80° C., pH 4.5, proceeds readily to give an equilibrium mixture containing somewhat more than 60% glucose, with equilibrium being attained within about 3.5 hours. However, when a solution which was the product mixture arising from hydrocyanation of L-arabinose and which contained, inter alia, L-mannose and L-glucose was treated with molybdate under identical conditions there was no measurable epimerization even after 22 hours. In fact, equilibration of the epimers within 5 hours was not achieved until molybdate concentration reached 11,000 ppm! Even with an equilibration time of 22 hours the required molybdate concentration was 5,000 ppm. Subsequeent investigation demonstrated that these results arose from the presence of inhibitors in the feedstock when the latter was the product mixture arising in the preparation of L-glucose from L-arabinose via hydrocyanation. That is, L-glucose formation, especially in a hydrocyanation-hydrogenation-hydrolysis sequence, was accompanied by other components acting as inhibitors in the molybdate-catalyzed epimerization of mannose to glucose. Because L-arabinose provides the most feasible entry into the L-glucose system, the presence of these inhibitors appears virtually assured regardless of the particular preparative scheme used for L-glucose production. Pragmatically this fact required us to overcome the aforementioned inhibitory effects and much of our subsequent work was directed toward solving this problem. Although the nature of the inhibitors is not known with certainty and their relative importance is unknown, both gluconamide and cyanide are believed to be present and both were shown to exhibit inhibitory effects.

Our solution to overcoming the observed inhibition was aided by two key observations. One observation was that inhibition decreased with decreasing pH. The other, perhaps more import observation, is that the inhibitory effect appeared to be largely ameliorated at higher temperatures. On the basis of these observations it was possible to effect epimerization with molybdate with desirable low concentrations, i.e., under about 1,500 ppm, and within just severl hours.

The feedstocks of this invention are product mixtures arising from the hydrocyanation of L-arabinose. In particular, the feedstocks are product mixtures arising from a hydrocynation-hydrogenation-hydrolysis sequence starting from L-arabinose, because the cyanohydrins resulting from hydrocyanation are most readily converted to their corresponding hexoses via a hydrogenation-hydrolysis sequence. However, it appears that the inhibitors so detrimental to molybdate-catalyzed epimerization arise largely during hydrocyanation, so that feedstocks arising from hydrocyanation of L-arabinose where the cyanohydrins are converted to the L-hexoses via a sequence other than hydrogenation-hydrolysis are explicitly included in our invention. It is also contemplated that the feedstock may be one arising from separation of a mixture of L-glucose and L-mannose, where the mixture arises from hydrocyanation of L-arabinose and where the separation may be conducted by any convenient means, as by chromatographic separation or crystallization.

The feedstocks may contain up to about 50% dry solids. It is desirable that the feedstock be as concentrated as is possible to minimize the total volume of solution which must be processed. Of the dry solids, mannose may constitute anywhere up to about 99%, although typically reaction product mixtures will contain mannose in the range from about 40 to about 80%. However, the method of epimerization as described is applicable independent of the mannose percentage. The arabinose content of the feedstock may be as low as 0.5% and as high as about 12% of the dry solids present, buy typically it will be in the range from about 2 to about 10% by weight of the total dry solids.

Any molybdate which is sufficient soluble in the epimerization feedstock under epimerization conditions to give at least about 1,500 ppm molybdate may be used in the practice of this invention. Sodium and potassium molybdate, $Na_2MoO_4$ and $K_2MoO_4$, resp., are examples of quite water-soluble molybdates which may be used in the practice of this invention. Molybdenum trioxide also may be used even though it is generally not thought of as a soluble molybdate, but it does dissolve in the epimerization feedstock under epimerization conditions to afford about 1,500 ppm molybdate. Other suitable species which may be used in the practice of this invention include iron molybdate, calcium molybdate, ammonia molybdate, molybdenum dioxide, and molybdenum (VI) oxide bis (2,4-pentanedionate).

To effect epimerization a soluble molybdate concentration affording under about 1,500 ppm molybdenum is sufficient, and concentrations between about 200 and about 1,000 ppm are preferred. It needs to be clearly understood that soluble molybdate concentrations affording in excess of 1,500 ppm molybdenum may be used without detriment but also without substantial benefit. It has been found essential to conduct epimerization at a pH under 3.0 to overcome the inhibitory effects of the poisons present in the feedstock. This was a surprising result in light of U.S. Pat. No. 4,029,878, where the patentee cautions against epimerization at a pH less than 3. The lower pH limit under which epimerization is conducted depends somewhat on epimerization temperature which usually will be in the range of 75°–100° C. It is preferred that epimerization be conducted at a pH from about 1.3 to about 2.7, with lower temperatures favoring a lower pH. Practical considerations dictate that epimerization conditions be chosen to give a reaction time no greater than about 20 hours, and preferably no more than about 10 hours. This time range results from the desire to minimize byproducts attending epimerization, including materials which impart color to the epimerization mixture. In practice, it is desirable to conduct epimerization for a time somewhat less than that necessary to attain equilibrium. For example, 90% of the equilibrium L-glucose level may be attained in about one-half the time necessary to attain equilibrium, and the economies of reduced reaction time far outweight the cost of reduced L-glucose conversion. Pragmatically, it is most economical to conduct the epimerization for a time to afford a ratio of L-glucose to L-mannose of at least 1.0.

The process which is our invention can be readily described as follows. A feedstock arising from hydrocyanation of L-arabinose and containing at least 40% L-mannose on a dry solids basis is epimerized with soluble molybdate in an epimerization reactor. Soluble molybdate will be present in a concentration to afford up to about 1,500 ppm molybdenum, but the latter most desirably will be in the range between about 200 and 1,000 ppm molybdate. Epimerization will be conducted at a temperature generally between about 75° and about 100° C., even more desirably between 80° and 95° C., and at a pH under about 3.0, and usually between about 1.3 and about 2.7, for a time sufficient to achieve the desired degree of epimerization. It is desirable to remove molybdate prior to separation of the hexoses from the epimerized feedstock, most desirably by contacting the epimerized feedstock with a material which removes molybdate by ion exchange, usually an ion exchange resin. Anion exchange resins of the styrene-divinylbenzene type in their strong base form are quite suitable. Since it is often sought to minimize all ion content, the feedstock may be treated with both an anion and cation exchange resin prior to chromatographic separation. In one embodiment, after epimerization is complete the epimerized mixture is sent to an ion exchange column to remove molybdate. The molybdate-free mixture is then used as the feedstock for a chromatographic separator which produces a stream enriched in L-glucose and a stream depleted in the latter sugar. U.S. Pat. No. 4,471,114 and U.K. Pat. No. 1,540,556 are illustrative of such a separation. The L-glucose depleted stream will be simultaneously enriched in L-arabinose and this stream may be recycled to the epimerization reactor by admixture with its incoming feedstock. The stream enriched in L-glucose is separately recovered.

In other applications it may be desirable to epimerize a feedstock virtually depleted in L-glucose. For example, where a reaction product mixture contains predominantly L-glucose, it may not be cost effective to equilibrate that mixture prior to separation of L-glucose from L-mannose. In such a case, after separation the stream containing largely L-mannose with from 0.5 to about 12% of L-arabinose may be separately epimerized with molybdate and, after removal of molybdate, be used as part of, or as a separate, feedstock to the separation unit. Other variations are possible and will be recognized by those skilled in this art.

The examples which follow are only illustrative of this invention and are not intended to limit it in any way thereby.

EXAMPLE 1

Epimerization of L-mannose

An aqueous solution containing 9.7% wt. % L-mannose, 0.8% wt. % L-arabinose, and 0.2% L-glucose was used as the feed for epimerization. To 500 g. of this solution was added 0.78 g sodium molybdate to afford a solution containing 600 ppm Mo. The pH was adjusted to 5.0 by addition of sulfuric acid, and the solution was heated at 80° C. After 7 hours virtually no epimerization had occurred, and an additional 7.3 g sodium molybdate was added to afford a total of 6400 ppm Mo. in solution. The solution was pH adjusted to 5.0 and again heated to 80° C. Complete results are tabulated below.

TABLE 1

Epimerization of L-Mannose at 80° C. in Feedstock Containing L-Arabinose.

| Mo, ppm | Time (hours) | Product Composition, % | | |
|---|---|---|---|---|
| | | glucose | arabinose | mannose |
| 600 | 0 | 1.3 | 7.0 | 91.7 |
| | 1.0 | 1.3 | 6.7 | 91.8 |
| | 2.5 | 2.2 | 6.9 | 91.0 |
| | 3.75 | 2.3 | 7.1 | 90.6 |
| | 6.0 | 2.5 | 6.8 | 90.7 |
| | 7.0 | 2.3 | 6.9 | 90.8 |
| 6400 | 0 | 2.5 | 6.7 | 89.1 |
| | 1.0 | 11.8 | 7.0 | 81.2 |
| | 2.75 | 25.2 | 6.6 | 68.2 |
| | 4.5 | 33.1 | 6.4 | 56.7 |
| | 7.0 | 44.3 | 6.4 | 45.2 |
| | 22.0 | 65.2 | 5.6 | 26.3 |

A control experiment using a feedstock of pure D-mannose containing 600 ppm Mo at pH 4.5 showed epimerization occurred readily, affording 50:50 mixture of glucose:mannose in about 2.5 hours, and a 60:40 mixture in about 4 hours. In contrast, the table shows no significant epimerization of mannose in the feedstock at 600 ppm Mo even after 7 hours at 80° C. and even with 6400 ppm Mo—a 10-fold greater concentration—a 50:50 mixture was obtained only after 7 hours (3 times longer reaction time).

EXAMPLE 2

Effect of pH in overcoming poisons

To 20 mL of an aqueous feedstock containing 12.6 wt. % L-mannose, 0.07 wt. % L-glucose, and 0.5 wt. % L-arabinose was added sodium molybdate in an amount calculated to afford the desired concentration of Mo. Solutions were adjusted to their desired pH by addition of 10% sulfuric acid and epimerization was followed with time. From the resulting plots of time glucose yield the time for conversion to a 60:40 glucose:mannose mixture (60% yield) was determined. The times as a function of temperature, Mo concentration, and pH are summarized in Table 2.

TABLE 2

Effect of pH, Molybdenum Concentration, and Temperature on Epimerization Time for 60% Glucose Yield.

| T, °C. | pH | Mo concentration, ppm | Time (hours) |
|---|---|---|---|
| 80 | 1.8 | 2000 | 4.5 |
|  |  | 1250 | 9.0 |
|  |  | 500 | 17.0 |
|  | 2.3 | 2500 | 4.0 |
|  |  | 1500 | 11.0 |
|  |  | 750 | 23.0 |
|  | 3.0 | 2500 | 13.0 |
|  |  | 1500 | 35.0 |
| 95 | 2.3 | 1250 | 1.75 |
|  |  | 500 | 7.0 |
|  | 3.0 | 2500 | 1.5 |
|  |  | 1500 | 3.9 |
|  |  | 750 | 9.5 |

Figure 2:
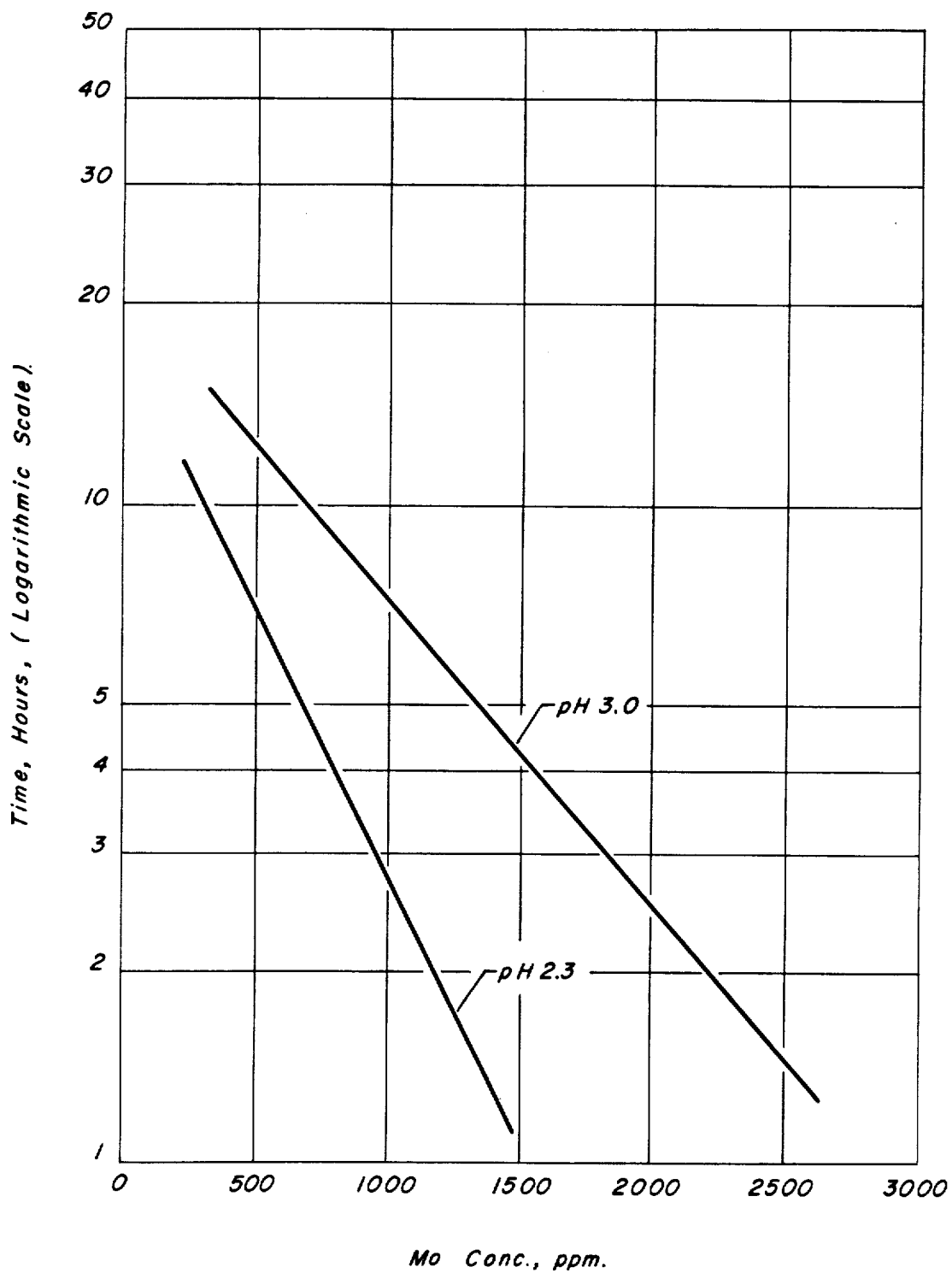

These data show that if reaction times are limited to 10 hours, epimerization at 80° C. must be conducted at a pH under about 2.3 if reasonable (no more than about 1500 ppm) amounts of Mo are used, whereas at 95° C. the pH must be 3.0 or less. FIGS. 1 and 2 summarize these data and present the results graphically.

EXAMPLE 3

Identification of Poisons

To demonstrate the inhibitory (poisoning) effect of materials known or reasonably expected to be in the epimerization feedstock, different substances were added to solutions of pure mannose prior to epimerization. Molybdate was used at a concentration affording 500 ppm molybdenum, and epimerization was conducted at 95° C. at pH 2.3. These conditions of temperature and pH were found to be quite effective in overcoming the inhibitory effects of poisons in the product mixture arising from the cyanide addition to L-arabinose. Hence, the inhibitory effects manifested in this example demonstrates the intensity or extent of inhibition exhibited by the added substances.

Figure 3:
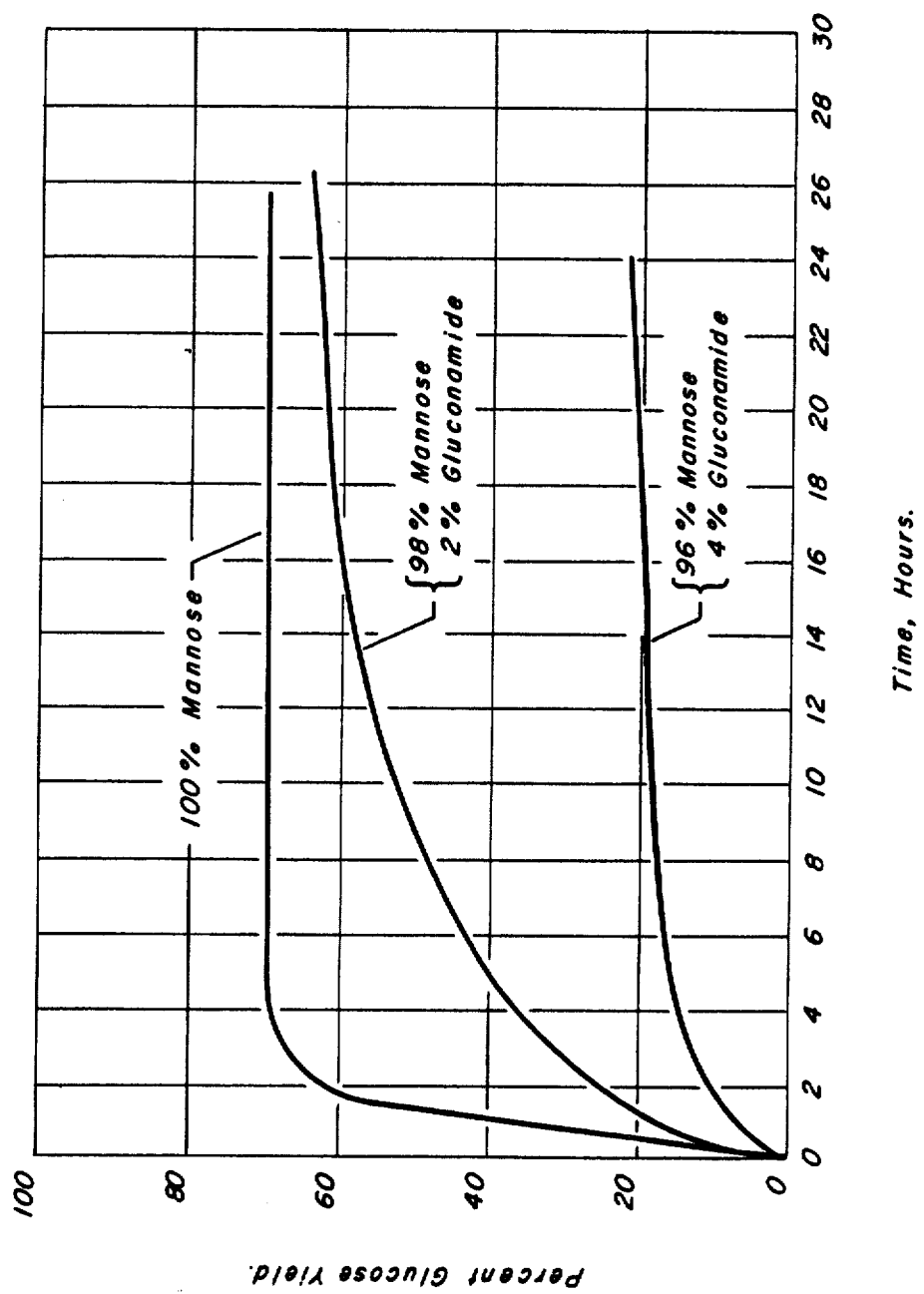
FIGS. 3 and 4 show the inhibition to epimerization arising from two species usually present in the product mixture from hydrocyanation-hydrogenation-hydrolysis of L-arabinose.
Figure 4:
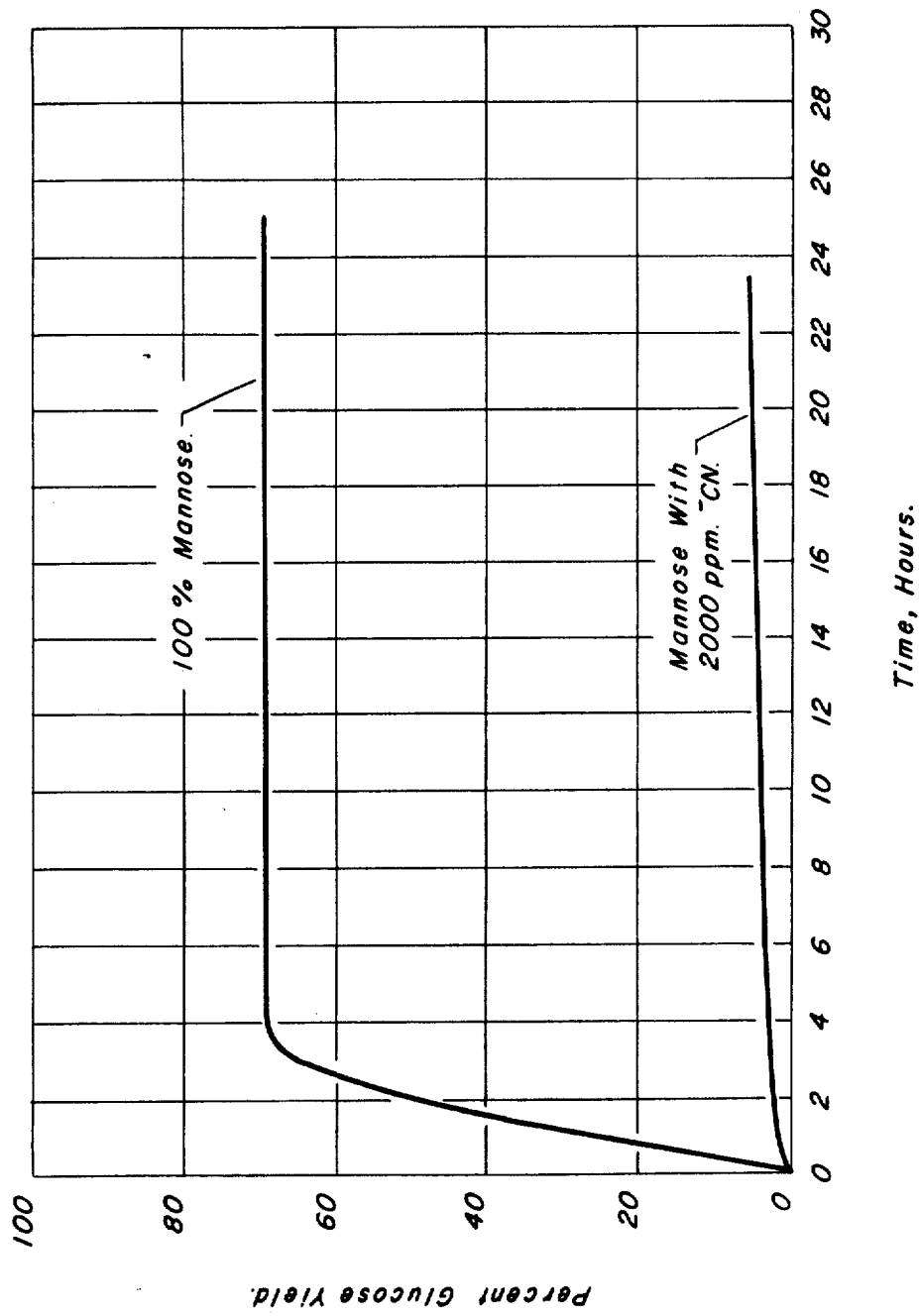

FIG. 3 shows the inhibitory effects of gluconamide and FIG. 4 shows similar effects accompanying cyanide. Both show powerful retardation of epimerization even when they are present at relative low concentration.

What is claimed is:

1. A method of enhancing the yield of L-glucose from an aqueous mixture containing at lest about 40 percent by weight L-mannose on a dry solids basis and containing molybdate epimerization inhibitors, said mixture containing inhibitors arising from the hydrocyanation of L-arabinose, where the method comprises catalyzing the epimerization of L-mannose to L-glucose with a solution of a molybdate containing up to about 1500 parts per million molybdenum at a pH below 3.0 and at a temperature between about 75 and about 100° C. for a time sufficient to give a ratio of L-glucose to L-mannose of at least 1.

2. The method of claim 1 where the aqueous mixture contains up to about 50% by weight dry solids.

3. The method of claim 1 where the aqueous mixture contains from about 40 to about 80% by weight mannose.

4. The method of claim 1 further characterized in that the aqueous mixture contains from about 2 to about 10% by weight arabinose.

5. The method of claim 1 where the epimerization is catalyzed by said molybdate at a concentration giving between about 200 and about 1,000 ppm molybdenum.

6. The method of claim 1 where the pH of epimerization is between about 1.3 and about 2.7.

* * * * *

UNITED STATES PATENT AND TRADEMARK OFFICE
CERTIFICATE OF CORRECTION

PATENT NO. : 4,718,405
DATED : January 12, 1988
INVENTOR(S) : Firth et al.

It is certified that error appears in the above-identified patent and that said Letters Patent is hereby corrected as shown below:

In Column 8, line 11: Change "lest" to --least--.

Signed and Sealed this

Seventh Day of June, 1988

Attest:

DONALD J. QUIGG

*Attesting Officer*  *Commissioner of Patents and Trademarks*